United States Patent [19]

Nakamura et al.

[11] Patent Number: 4,994,377
[45] Date of Patent: Feb. 19, 1991

[54] METHOD FOR ASSAYING 1,5-ANHYDROGLUCITOL AND KIT THEREFOR

[75] Inventors: Tsuneo Nakamura, Saitama; Hiroshi Akanuma, Kanagawa; Masahiko Yabuuchi, Saitama; Kazuo Kato, Saitama; Minoru Masuda, Saitama, all of Japan

[73] Assignee: Nippon Kayaku Kabushiki Kaisha, Tokyo, Japan

[21] Appl. No.: 98,508

[22] Filed: Sep. 18, 1987

[30] Foreign Application Priority Data

Sep. 22, 1986 [JP] Japan ................... 61-222003

[51] Int. Cl.$^5$ .............. C12Q 1/26; C12Q 1/28; G01N 1/00
[52] U.S. Cl. ................................ 435/25; 435/28; 435/803; 435/105; 435/810; 436/174; 436/175; 436/178
[58] Field of Search ............ 435/25, 28, 14, 803, 435/810, 105, 26; 436/85, 174, 175, 178

[56] References Cited

U.S. PATENT DOCUMENTS 4,810,640  3/1989  Nakamura et al. ............ 435/25

OTHER PUBLICATIONS

Journal of Biochemistry, vol. 99, No. 3, 1986, pp. 607–613.
Enzyme Nomenclature, Academic Press, pp. 56–57 (1978).
Janssen, F. W. et al., Biochemica et Biophysica Acta, vol. 167, pp. 501–510 (1968).
Ruelius, H. W. et al., Biochimica et Biophysica Acta, vol. 167, pp. 493–500 (1968).
Yamada, Y. et al., The Journal of Biochemistry, vol. 62, No. 2, pp. 223–228 (1967).

Primary Examiner—Esther L. Kepplinger
Assistant Examiner—Toni R. Scheiner
Attorney, Agent, or Firm—Henry C. Nields

[57] ABSTRACT

This invention relates to a novel method for assaying 1,5-anhydroglucitol, which is expected to serve as a marker for diabetes, and a kit therefor. More particularly, it relates to:
(1) a method for assaying 1,5-anhydroglucitol, which comprises selectively removing sugars from a specimen containing 1,5-anhydroglucitol; allowing pyranose oxidase or L-sorbose oxidase to act on 1,5-anhydroglucitol contained in the sample thus obtained in the presence of oxygen; and determining 1,5-anhydroglucitol from the amount of the hydrogen peroxide thus formed; and
(2) a reagent kit for assaying 1,5-anhydroglucitol which comprises an agent for removing sugars, a reagent for detecting hydrogen peroxide and an enzyme for oxidizing 1,5-anhydroglucitol.

10 Claims, 2 Drawing Sheets

METHOD FOR ASSAYING 1,5-ANHYDROGLUCITOL AND KIT THEREFOR

1. FIELD OF THE INVENTION

This invention relates to a method for assaying 1,5-anhydroglucitol (abbreviated to 1,5-AG hereinafter), which is expected to serve as a marker for the diagnosis of diabetes, with the use of an enzyme, as well as a kit for assaying the same.

2. BACKGROUND OF THE INVENTION 1,5-AG is present in human cerebrospinal fluid and plasma and it has been reported that its quantity is reduced in plasma with certain diseases, particularly with diabetes. 1,5-AG has been conventionally assayed mainly by gas chromatography (see, e.g., Yoshioka et al., Tonyobyo, 25, 1115–1118 (1982)).

However known methods for assaying 1,5-AG have some disadvantages from the clinical viewpoint such that it is necessary to preliminarily treat a specimen and to label 1,5-AG; that the maintenance of analytical instruments requires troublesome procedures and should be carried out by an experienced person; and that gas chromatographic analysis requires a prolonged period of time, which makes it difficult to assay a number of specimens.

Under these circumstances, we have attempted to develop a method by which a number of specimens can be readily assayed, thus completing the present invention.

3. SUMMARY OF THE INVENTION

Pyranose oxidase and L-sorbose oxidase have been known each as an enzyme capable of oxidizing a sugar. We have unexpectedly found that these enzymes would also oxidize 1,5-AG, which is a sugar alcohol; and that they can be used in assaying 1,5-AG in a blood sample from which sugars have been selectively removed.

Thus the present invention has been completed based on the above findings. Accordingly, the present invention relates to a method for assaying 1,5-AG which comprises selectively removing sugars present in a specimen; allowing pyranose oxidase or L-sorbose oxidase to act on 1,5-AG contained in the sample thus obtained; and determining 1,5-AG from the amount of the hydrogen peroxide thus formed, as well as a reagent kit for assaying 1,5-AG which comprises an agent for removing sugars, a reagent for detecting hydrogen peroxide and an enzyme for oxidizing 1,5-AG.

The method of the present invention makes it possible to assay a number of specimens without requiring any complicated labeling operation like conventional gas chromatographic analyses. Further it is not necessary in the method of the present invention to maintain and control advanced analytical instruments.

4. BRIEF DESCRIPTION OF THE DRAWINGS

5. DETAILED DESCRIPTION OF THE INVENTION

Figure 1:
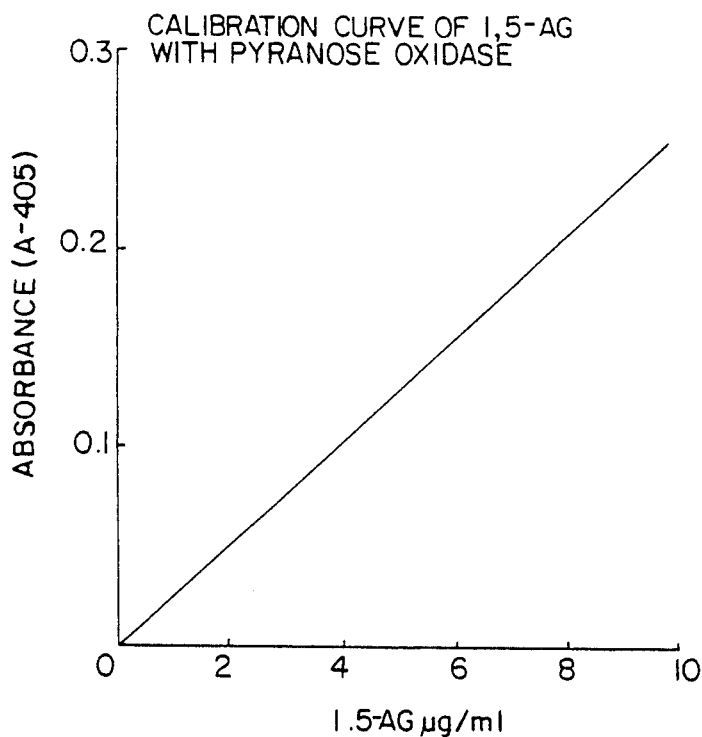
FIG. 1 shows a calibration curve for determining 1,5-AG with the use of pyranose oxidase.

Now the first aspect of the present invention will be described.

Any specimen may be used in the present invention without limitation, so long as it is required to assay 1,5-AG contained therein. Examples of the specimen include cerebrospinal fluid, plasma, serum and urine. These specimens contain sugars such as glucose capable of reacting with pyranose oxidase or L-sorbose oxidase. Thus these sugars should be removed from the specimens to give appropriate samples.

The pyranose oxidase and L-sorbose oxidase to be used in the present invention are not strictly limited, so long as they fall within the categories of EC 1.1.3.10 and EC 1.1.3.11, respectively, as determined by IUPAC=IUB Nomenclature Committee. For example, pyranose oxidase produced by *Polyporus obtusus* ATCC 26733 and L-sorbose oxidase produced by *Trametes sanguinea* IFO 4923 may be used.

These enzymes are usually used in the form of a solution in a buffer. Alternately they may be used in the immobilized form onto carriers through conventional techniques such as covalent bonding or adsorption. Examples of the carriers include a membrane, gel, particulate, microcapsular, tubular or container type. The amount of an enzyme to be used varies depending on, for example, the amount of a sample. Generally 0.5 units or more, preferably 1.5 to 5 units, of the enzyme may be used in order to complete the enzymatic reaction within a desirable period of time. It is not always required that the enzyme has the highest purity, although a higher specific activity of the enzyme is more desirable for the reaction, as a matter of course.

The pyranose oxidase and L-sorbose oxidase to be used in the present invention may be obtained according to the methods disclosed in Biochim. Biophys. Acta, 167, 493–500 (1968) and J. Biochem., 62 (2), 223–229 (1967), respectively.

The method of the present invention may be carried out, for example, in the following manner. Namely, an electron acceptor and 0.5 to 10 units/ml, preferably 1 to 5 units/ml, of pyranose oxidase or L-sorbose oxidase are added to a specimen and the obtained mixture is incubated at 4° to 50° C., preferably 25° to 40° C., for 0.5 to 3 hours, preferably 0.5 to 1 hour. The hydrogen peroxide thus formed is then determined and the amount of 1,5-AG may be determined therefrom by using a calibration curve which has been preliminarily formed. Now the method of the present invention will be described in detail.

Any method may be employed for detecting hydrogen peroxide in the method of the present invention, so long as it is highly sensitive. Among a number of available methods, it is the most commonly employed to oxidize various substrates with hydrogen peroxide by using horseradish peroxidase (HRP) as a catalytic enzyme. Then the colored substance fluorescent substance or chemiluminescence thus formed by the oxidation may be determined by measuring the absorbance, by fluorometry or by photometry, respectively. Examples of the substrate for HRP capable of forming a colored substance include 2,2'-azinobis(3-ethylbenzothiazoline-6-sulfonic acid (ABTS), o-phenylenediamine (OPD), 5-aminosalicylic acid (5-AS) and 3,3',5,5'-tetramethylbenzidine (TMB). Examples of the substrate for HRP capable of forming a fluorescent substance include p- hydroxyphenylacetic acid and 3-(p-hydroxyphenyl)-propionic acid (HPPA). Examples of the substrate for HRP capable of showing chemiluminescence include luminol and isoluminol.

0.3 ml of a sodium phosphate buffer solution (1/15 M, pH 5.6), 0.5 ml of a coloring solution containing 4 mM of 2,2'-azinobis(3-ethylbenzothiazoline6-sulfonic acid (ABTS) and 12 units/ml of horseradish peroxidase, 0.1 ml of a 25 units/ml solution of pyranose oxidase or L-sorbose oxidase and 0.1 ml of a solution of 1,5-AG are introduced into a vessel and allowed to react at 37° C. for 30 minutes. Then the reaction is ceased by ice-cooling and the absorbance of the reaction mixture at 405 nm is measured. Then the concentration of the 1,5-AG is determined from the absorbance of the sample by using a calibration curve which has been preliminarily formed by using 1,5-AG solutions of known concentrations.

There have been known several methods for detecting hydrogen peroxide through chemiluminescence without using HRP, for example, by inducing the luminescence of luminol with hydrogen peroxide in the presence of a ferricyanide ion; by inducing the luminescence of lucigenin with hydrogen peroxide in the presence of a metal ion; and by reacting an aryl oxalate such as bis(2,4,6-trichlorophenyl) oxalate with hydrogen peroxide in the presence of a fluorescent substance to thereby excite the fluorescent substance with the decomposition energy of the oxalate, thus giving luminescence. Alternately, a hydrogen peroxide electrode may be employed in order to directly detect hydrogen peroxide.

Now the removal of sugars from a specimen will be described.

As a result of our studies on the removal method of sugars, we have found that sugars can be selectively removed in such a manner as to completely leave 1,5-AG intact by treating a specimen with a strongly basic anion exchange resin or boric acid, thus giving a sample containing 1,5-AG.

When a strongly basic anion exchange resin is to be used, a specimen is slowly passed through said strongly basic anion exchange resin of OHtype to thereby adsorb and remove sugars. Preferred examples of the strongly basic anion exchange resin are those having a quaternary ammonium salt group, e.g., a trimethylamino group (type I) or a hydroxyethyldimethylamino group (type II), as an ion exchange group. Since this method depends on the flow rate of the specimen solution through the resin, it is preferable to dress the resin particles through 200-mesh to 400-mesh sieves in order to slowly pass the specimen therethrough. The specimen may be further treated with a cation exchange resin to thereby neutralize the same.

Cation exchange resins are various anionic resins of H-type. The anionic resins include those of any cation exchange resins ranging from strongly acidic ones to weakly acidic ones. It is particularly preferable to use, for example, a strongly acidic cation exchange resin of H-type having a sulfonate group.

When boric acid is to be used, the specimen may be treated with boric acid per se. However it is preferred to use a resin to which boric acid is bound.

Examples of the resin to which boric acid is bound are a borate covalent bond resin and a borate type anion exchange resin.

Borate type anion exchange resins are various cationic resins of borate type. The cationic resins include any anion exchange resins ranging from strongly basic ones to weakly basic ones. It is particularly preferable to use, for example, a strongly basic anion exchange resin of borate type having a tri($C_1$-$C_4$)alkylamino (i.e. trimethylamino) group (type I) or a hydroxy($C_1$-$C_4$)alkyl-di($C_1$-$C_4$)alkylamino (i.e. hydroxyethyldimethylamino) group (type II), and a intermediate basic anion exchange resin of borate type having both di($C_1$-$C_4$)alkylamino (i.e. dimethylamino) group and hydroxy($C_1$-$C_4$)-alkyldi($C_1$-$C_4$)alkylamino (i.e. hydroxyethyldimethylamino) group such as Bio-Rex 5 (borate type).

When a specimen treated with boric acid is to be used as a sample, it is preferable to further treat the specimen with an anion exchange resin optionally together with a cation exchange resin in order to remove residual complexes of boric acid with sugars present therein.

Anion exchange resins are various cationic resins of OH— or weakly acidic salt type. The cationic resins include any anion exchange resins ranging from strongly basic ones to weakly basic ones. As the weak acids forming the weak acid salts of these cationic resins, carbonic acid and an organic acids such as formic and acetic acids are preferable. It is particularly preferable to use a strongly basic anion exchange resin having a trimethylamino group (type I) or a hydroxyethyldimethylamino group (type II). As the cation exchange resin, those described above may be used.

The boric acid treatment for removing sugars may be carried out in the following manner. When boric acid per se is to be used, an aqueous solution of boric acid is added to a specimen such as plasma to such an extent as to prevent the boric acid from leaking in the subsequent anion exchange resin treatment step, followed by stirring. Then the mixture is passed through a column packed with an anion exchange resin optionally together with a cation exchange resin.

When a resin to which boric acid is bound is to be used, said resin is packed in a column together with an anion exchange resin and a cation exchange resin in such a manner as to place the boric acid resin at the top in the column. Then a specimen may be passed through the above column.

In addition to the above methods, sugars in a sample may be selectively removed by utilizing an extreme chemical stability of 1,5-AG or by modifying glucose, which is the major contaminant of 1,5-AG, with the use of an enzyme as a catalyst. The former method may be carried out, for example, by heating a sample in the presence of 6 N hydrochloric acid to thereby decompose sugars other than 1,5-AG and then recovering the 1,5-AG remaining in the decomposition products; or by treating a sample with a reducing agent such as sodium borohydride to thereby reduce sugars having carbonyl or formyl groups other than 1,5-AG, thus giving modified compounds which can not react with pyranose oxidase or L-sorbose oxidase. On the other hand, the latter methods may be carried out by, for example, converting glucose into gluconic acid with glucose oxidase (EC 1.1.3.4) or into glucose 6-phosphate with hexokinase (EC 2.7.1.1). None of these compounds modified with an enzyme can react with pyranose oxidase or L-sorbose oxidase. Thus 1,5-AG which remains intact in the enzymatic treatment may be determined in the abovementioned manner.

In the second aspect, the present invention provides a reagent kit which comprises an agent for removing sugars, a reagent for detecting hydrogen peroxide and an enzyme for oxidizing 1,5-AG.

As described above, examples of said agent for removing sugars include boric acid, a resin to which boric acid is bound, a strongly basic anion exchange resin, sodium borohydride, glucose oxidase, hexokinase, an anion exchange resin and a cation exchange resin. Among these agents, a resin to which boric acid is bound, an anion exchange resin combined with a cation exchange resin, and an anion exchange combined with a strongly basic anion exchange resin and a cation exchange resin, are preferable from the viewpoint of convenience in operation. When incorporating into a kit, these agent may be usually packed in a small disposable column in such a manner as to place the resin to which boric acid is bound or the strongly basic anion exchange resin at the top.

Any enzyme may be used without limitation in the determination of 1,5-AG, so long as it can be directly used in the determination of 1,5-AG. For example, pyranose oxidase or L-sorbose oxidase may be used. Examples of the reagent for detecting hydrogen peroxide include combinations of a peroxidase or a peroxidase-like active substance with a coloring substrate or a colorant and a coupler; a peroxidase and a fluorescent substrate; a peroxidase and a luminescent substrate; and a ferricyanide ion and a luminescent substrate. Particular examples of these reagents are obvious from the methods for detecting hydrogen peroxide as described above.

The enzyme for oxidizing 1,5-AG and the detection reagent may be mixed together to give a single reagent. Alternately, these ingredients may be appropriately divided, when they would affect each other. They may be formulated into solution(s) or powder(s). Further they may be carried by an appropriate material such as a filter paper or film to give an analytical paper or film.

In addition to the combined reagents, the assay kit of the present invention may further comprise an agent for removing proteins, such as perchloric acid, and standard reagent(s) containing a given amount of 1,5-AG.

The amount of the agent for removing substrates other than 1,5-AG may be as follows. When a strongly basic anion exchange resin is to be used, 0.1 to 1.0 ml of the strongly basic anion exchange resin of OH-type may be combined with 0.01 to 0.5 ml of a cation exchange resin and the total amount of the resins may be appropriately adjusted to 0.2 to 1.5 ml. When a resin to which boric acid is bound is to be used, 0.1 to 0.5 ml of the resin to which boric acid is bound may be used together with 0.1 to 1.0 ml of an anion exchange resin and 0.01 to 0.5 ml of a cation exchange resin and the total amount of the resins may be appropriately adjusted to 0.5 to 2 ml.

The amount of the enzyme for determining 1,5-AG in the kit varies depending on the number of samples to be assayed, e.g., 100 or 300 samples. Usually 0.5 to 10 units of the enzyme may be used per sample. When HRP and ABTS are to be used as the reagent for detecting hydrogen peroxide, 10 m units to 100 units per sample of HRP and 0.5 to 10 μM per sample of ABTS are incorporated in the kit.

In addition thereto, the kit may further contain 5 to 20 μg per sample of perchloric acid, in terms of purity of 100%, for removing proteins and 200 to 2000 μg of 1,5-AG as samples for forming a calibration curve.

To further illustrate the present invention, the following Examples will be given.

EXPERIMENTAL EXAMPLE 1

Calibration curve of 1,5-AG with the use of pyranose oxidase

ABTS and HRP were dissolved in a 1/15 M phosphate buffer solution (pH 5.6) to give concentrations of 4 mM and 12 units/ml, respectively. To 0.5 ml of the coloring solution thus obtained, 0.1 ml of a standard 1,5-AG solution, 0.3 ml of a 1/15 M phosphate buffer solution and 0.1 ml of a 5 mg/ml solution of pyranose oxidase (mfd. by Takara Shuzo Co., Ltd.; specific activity to glucose: 5 units/mg) were added and the obtained mixture was allowed to react at 37° C. for one hour. FIG. 1 shows a calibration curve formed by measuring the absorbance of the above reaction mixture at 405 nm.

EXPERIMENTAL EXAMPLE 2

Calibration curve of 1,5-AG with the use of L-sorbose oxidase

Figure 2:
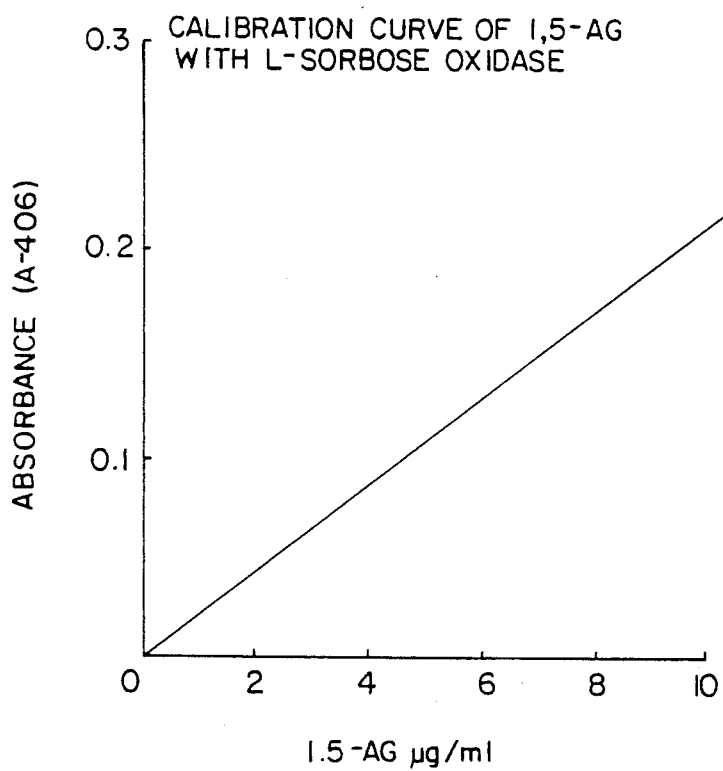
FIG. 2 shows a calibration curve for determining 1,5-AG with the use of L-sorbose oxidase.

The procedure of Experimental Example 1 was followed except that the pyranose oxidase solution was replaced with a 5 mg/ml solution of L-sorbose oxidase (specific activity to glucose: 4.3 units/mg) to thereby form a calibration curve of 1,5-AG. FIG. 2 shows the result.

EXAMPLE 1

Assay of 1,5-AG with the use of pyranose oxidase

A model sample containing 1 mg/ml of glucose and 0.1 mg/ml of 1,5-AG was prepared. The model sample was subjected to the following pretreatments 1 to 5 to remove glucose therefrom. Then the remaining 1,5-AG was determined by the same method as the one described in Experimental Example 1. Assay of 1,5-AG was carried out by using a calibration curve which had been formed by subjecting each standard 1,5-AG solution to the same treatment as that employed in the case of the model sample. Table 1 shows the results.

(1) Removing substrates other than 1,5-AG as complexes with boric acid 0.02 ml of a 0.8 M aqueous solution of boric acid was added to 0.2 ml of a model sample and stirred. 0.1 ml of the supernatant of the resulting mixture was passed through a column packed with 0.5 ml of an anion exchange resin AG1-X8 (OH-type; mfd. by Bio-Rad Laboratories, Inc.) and the column was washed with 1.5 ml of distilled water to give 1.5 ml of an effluent.

(2) Removing substrates other than 1,5-AG by adsorbing the same by strongly basic anion exchange resin 0.2 ml of a model sample was passed through a column packed with 0.5 ml of an anion exchange resin AG1-X8 (OH-type, 400-mesh; mfd. by Bio-Rad Laboratories, Inc.) and the column was washed with 1.5 ml of distilled water to give 1.5 ml of an effluent.

(3) Removing substrates other than 1,5-AG through decomposition with hydrochloric acid To 0.2 ml of a model sample, 0.25 ml of 36% hydrochloric acid was added and the mixture was hermetrically sealed and heated to 110° C. for one day. The reaction mixture was evaporated to dryness to thereby remove the hydrochloric acid and the residue was redissolved in 0.2 ml of distilled water. 0.1 ml of the supernatant was passed through a column packed with 0.4 ml of an anion exchange resin AG1-X8 (acetate type) and 0.2 ml of a cation exchange resin (H-type) and the column was washed with 1.5 ml of distilled water to give 1.5 ml of an effluent.

(4) Reducing substrates other than 1,5-AG with sodium borohydride

To 0.5 ml of a model sample, 0.05 ml of a 40 mg/ml aqueous solution of sodium borohydride was added and the mixture was allowed to react at 37° C. for 30 minutes. Then the pH value of the reaction mixture was adjusted to 5 to 6 by adding 0.05 ml of a 60% aqueous solution of perchloric acid thereto to thereby decompose the residual sodium borohydride. To 0.1 ml of the supernatant of the reaction mixture, 0.2 ml of a 1.8% aqueous solution of barium hydroxide octahydrate and 0.2 ml of a 2% solution of zinc sulfate heptahydrate were added and the obtained mixture was centrifuged at 3,000 rpm for ten minutes. After removing the precipitate, a reduced sample was obtained.

(5) Oxidizing glucose with glucose oxidase

To 0.4 ml of a model sample, 0.2 ml of a 100 units/ml solution of glucose oxidase (mfd. by Boehringer Mannheim) was added and the obtained mixture was allowed to react at 37° C. for one hour. Then 0.2 ml of a 0.1 mg/ml catalase solution (mfd. by Sigma Co., LTD.) was added thereto and the mixture was allowed to react at 37° C. for five minutes to thereby completely decompose the hydrogen peroxide formed by the oxidation of the glucose.

Then the mixture was heated in boiling water for five minutes in order to inactivate and remove the glucose oxidase and catalase. After centrifuging the same at 3,000 rpm for ten minutes, a supernatant treated with glucose oxidase was obtained.

(6) Converting glucose into Glucose-6-phosphate with hexokinase

To 0.1 ml of a model sample, 0.2 ml of a 1.8% aqueous solution of barium hydroxide octahydrate and 0.2 ml of a 2% aqueous solution of zinc sulfate heptahydrate were added and the obtained mixture was stirred and centrifuged at 3,000 rpm for ten minutes. Thus a supernatant free from proteins was obtained. To 0.2 ml of the supernatant, 0.64 ml of a 0.1 M phosphate buffer solution (pH 7.0), 0.1 ml of a 0.2 M solution of magnesium chloride, 0.05 ml of a 0.2 M adenosine-5'-triphosphate (ATP) solution and 0.01 ml of a 1400 units/ml solution of hexokinase (mfd. by Boehringer Mannheim) were added and the obtained mixture was allowed to react at 37° C. for 30 minutes to give a treated sample.

EXAMPLE 2

Assay of 1,5-AG with the use of L-sorbose oxidase

The same model sample as the one used in Example 1 was treated in the same manner as that described in Example 1 to thereby remove glucose therefrom. Then the residual 1,5-AG was determined according to the method as described in Experimental Example 2. Table 1 shows the result.

TABLE 1

| | Assay of Model sample | |
|---|---|---|
| | Enzyme for determining 1,5-AG | |
| Method for removing glucose | pyranose oxidase | L-sorbose oxidase |
| (1) boric acid treatment | 99 μg/ml | 102 μg/ml |
| (2) strongly basic anion exchange resin treatment | 103 | 101 |
| (3) decomposition with hydrochloric acid | 101 | 97 |
| (4) reduction with sodium | 97 | 100 |

TABLE 1-continued

| | Assay of Model sample | |
|---|---|---|
| | Enzyme for determining 1,5-AG | |
| Method for removing glucose | pyranose oxidase | L-sorbose oxidase |
| borohydride | | |
| (5) glucose oxidase treatment | 112 | 108 |
| (6) hexokinase treatment | 103 | 101 |

EXAMPLE 3

Assay of 1,5-AG in serum with the use of pretreatment column 0.3 ml, 0.5 ml and 0.2 ml of ion exchange resins AG50W-X8 (H-type), AG1-X8 (OH-type) and AG1-X8 (borate type) (each mfd. by Rio-Rad Laboratories, Inc.), respectively, were packed in a small column from the bottom in this order to thereby give a pretreatment column.

Figure 3:
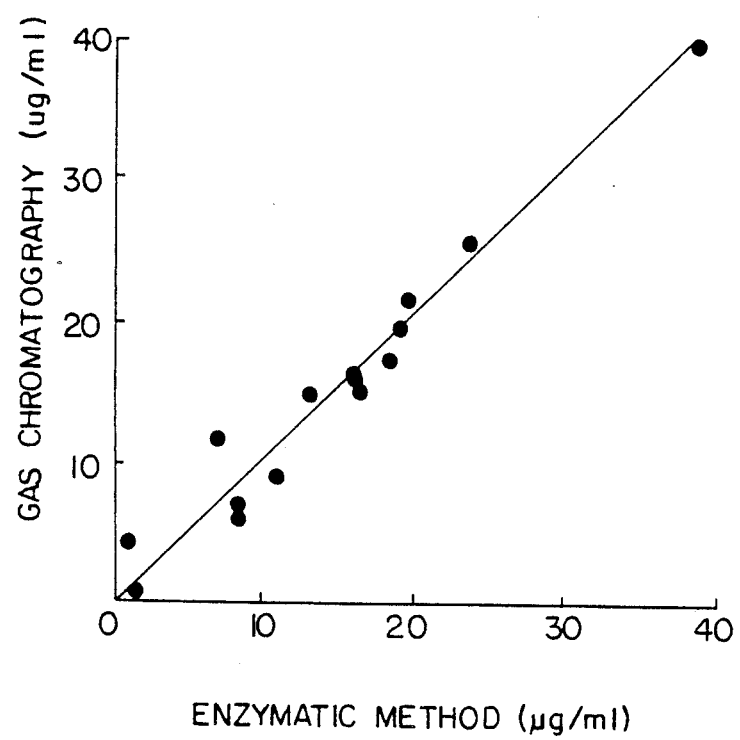
FIG. 3 shows a correlation between 1,5-AG values determined by an enzymatic method and those determined by a gas chromatographic method.

15 μl of a 60% aqueous solution of perchloric acid was added to 0.2 ml of human serum and the mixture was thoroughly shaken. After centrifuging the mixture to thereby remove proteins therefrom, 0.05 ml of the obtained supernatant was passed through the above-mentioned pretreatment column and the column was washed with 3 ml of distilled water to give 3 ml of an effluent. Then the effluent was evaporated to dryness and redissolved in 0.25 ml of distilled water to give a sample treated with the pretreatment column. The 1,5-AG remaining in the sample was determined according to the method as described in Experimental Example 1. Namely, a calibration curve formed by using standard 1,5-AG samples was employed. The correlation between the serum 1,5-AG values of normal and diabetic subjects thus determined and those of the same samples determined through gas chromatography is shown in FIG. 3. FIG. 3 obviously indicates that the data obtained by the method of the present invention correlates to those determined by the gas chromatographic method.

When the procedure of this Example was followed except that the AG1-X8 (borate type) was substituted by a boric acid gel, similar results to those as described above was obtained.

EXAMPLE 4

Assay of 1,5-AG in urine by using pretreatment column 10 ml of a human urine sample, from which proteins had been removed with a centrifugal ultrafiltration device Centricon 10 (mfd. by Amicon), was passed through a column packed with 1 ml each of ion exchange resins AG50W-X8 (H-type) and AG1X8 (acetate type) in this order and the column was washed with 6 ml of distilled water to give a desalted urine sample. The obtained sample was evaporated to dryness and redissolved in 0.5 ml of distilled water. Then it was passed through the same pretreatment column as the one described in Example 3 and the column was washed with 3 ml of distilled water to give 3.5 ml of an effluent from the pretreatment column. Then the treated liquor was evaporated and redissolved in 0.2 ml of distilled water to give a sample for assaying 1,5-AG. The assay of 1,5-AG was carried out by using 0.1 ml of the above sample according to the method as described in Example 1. For comparison, 1,5-AG in the residual sample was determined by gas chromatography. Table 2 shows the results.

TABLE 2

| | Assay of urine sample |
|---|---|
| Assay method | Human urine sample 1,5-AG conc. |
| enzymatic (pyranose oxidase) | 5.8 μg/ml |
| gas chromatography | 5.7 μg/ml |

EXAMPLE 5

Assay of serum 1,5-AG with the use of pretreatment column packed with borate resin A column was packed with 0.3 ml, 0.5 ml and 0.2 ml of ion exchange resins AG50W-X8 (H-type), AG1-X8 (OH-type) and AG1-X8 (borate type), each mfd. by Bio-Rad Laboratories, Inc. and having a particle size of 400-mesh, respectively from the bottom in this order to give a pretreatment column.

To 0.2 ml of human serum, 15 μl of a 60% aqueous solution of perchloric acid was added and the mixture was shaken and centrifuged to thereby remove proteins therefrom. 0.1 ml of the supernatant thus obtained was passed through the abovementioned pretreatment column and the column was washed with 3 ml of distilled water to give 3.1 ml of an effluent. This effluent was then evaporated to dryness. 1.0 ml of a reagent for detecting 1,5-AG was then added thereto and the mixture was allowed to react at 37° C. for one hour. The absorbance of this reaction mixture at 405 nm was measured and 1,5-AG was determined according to a calibration curve which had been preliminarily formed by treating standard 1,5-AG solutions in the same manner as the one employed in the case of human serum samples. The above reagent for detecting 1,5-AG was a 1/15 M phosphate buffer solution (pH 5.6) containing 2.5 units/ml of PROD, 60 m units/ml of HRP and 1 mM of ABTS.

The serum 1,5-AG values of normal and diabetic subjects thus determined closely correlate to those of the same samples determined by gas chromatography.

EXAMPLE 6

Assay of serum 1,5-AG with the use of pretreatment column packed with borate resin A small column was packed with 0.1 ml and 0.5 ml of ion exchange resins AG50W-X8 (H-Type) and Bio-Rex5 (borate type), each mfd. by Bio-Rad Laboratories, Inc. and having a particle size of 400-mesh, respectively in this order from the bottom to give a pretreatment column.

The procedure of Example 5 was followed except that the pretreatment column was replaced with this another one. The results thus obtained were similar to those of Example 5.

EXAMPLE 7

Assay of serum 1,5-AG with the use of pretreatment column packed with strongly basic anion exchange resin A small column was packed with 0.1 ml and 0.4 ml of ion exchange resins AG50W-X8 (H-type) and AG1-X8 (OH type), each mfd. by Bio-Rad Laboratories, Inc. and having a particle size of 400-mesh, respectively in this order from the bottom to give a pretreatment column.

To 0.2 ml of human serum, 15 μl of a 60% aqueous solution of perchloric acid was added and the mixture was immediately shaken and centrifuged to thereby remove proteins therefrom. 0.1 ml of the obtained supernatant was passed through the. above pretreatment column and the column was washed with 1.5 ml of distilled water to thereby give 1.6 ml of an effluent. The effluent was then evaporated to dryness and then treated in the same manner as the one described in Example 5 to thereby assay 1,5-AG. The results thus obtained were similar to those of Example 5.

EXAMPLE 8

Assay of serum 1,5-AG with the use of pyranose oxidase immobilized membrane

The pyranose oxidase as used in Example 1 was immobilized on a nitrocellulose film (pore size: 1 μm) in a conventional manner. Namely, 5 mg of pyranose oxidase (mfd. by Takara Shuzo Co., Ltd.; specific activity to glucose: 5 units/mg) and 5 mg of bovine serum albumin were dissolved in 0.5 ml of a 1/15 M phosphate buffer solution (pH 7.2) and 0.1 ml of a 1% glutaraldehyde solution was added thereto. The obtained solution was poured onto five nitrocellulose film sheets (pore size: 1 μm; diameter: 2 cm) and air-dried for day and night. Then each sheet was washed with 10 ml of a 1/15 M phosphate buffer solution (pH 6.0) to give a nitrocellulose film on which pyranose oxidase was immobilized.

This pyranose oxidase film was fitted to the surface of a hydrogen peroxide electrode (mfd. by Ishikawa Seisakusho, Ltd.) and 0.1 ml portions of standard 1,5-AG solutions of 1,5-AG concentrations of 1, 4, 16 and 32 μg/ml were passed therethrough under the following conditions:

mobile phase: 1/15 M phosphate buffer solution (pH 5.6); flow rate of mobile phase: 0.5 ml/min; and temperature: 25±1° C.

The amounts of the hydrogen peroxide thus formed were measured each as the area of the obtained peak and a calibration curve was formed therefrom.

Then the dry product obtained by evaporating ml of the effluent from the pretreatment column in Example 3 was dissolved in 0.25 ml of a 1/15 M phosphate buffer solution (pH 5.6). The resulting solution was passed through the above-mentioned electrode provided with the pyranose oxidase film in the same manner as employed in the case of the standards. The area of the peak thus obtained was measured and 1,5-AG was determined therefrom according to the above calibration curve.

Similar to the case of Example 3, the 1,5-AG values of normal and diabetic subjects closely correlate to those of the same sample determined by gas chromatography.

EXAMPLE 9

Reagent kit (1) Preparation of kit

Reagent A: 2.0 ml of a 60% solution of perchloric acid was introduced into a reagent vial.

Reagent B: 200 mg of PROD (5 units/mg; mfd. by Takara Shuzo Co., Ltd.), 0.24 mg of HRP (100 units/mg; mfd. by Wako Pure Chemicals Co., Ltd.) and 200 mg of ABTS (mfd. by Boehringer Mannheim) were dissolved in 100 ml of a 0.27 M sodium phosphate buffer solution (pH 5.6) in such a manner as to give a mixture capable of being contained in a single reagent vial and then lyophilized in a conventional manner.

Pretreatment column: A 1.5-ml reservoir (mfd. by Analytical International) provided with a fritted filter was packed with 0.1 ml of AG50W-X8 (H-type) and 0.4 ml of AG1-X8 (OH-type), both mfd. by Bio-Rad Laboratories, Inc., from the bottom in this order. Then a fritted filter was further provided on the packed resins to thereby fix the resins. A cap was provided over the outlet while the inlet was hermetically sealed in order to prevent the packed resins from being dried and to inhibit the permeation of carbon dioxide gas in the atmosphere, which would degrade the resins.

Standard solution: 0.2 ml of 1 mg/ml solution of 1,5-AG was introduced into a reagent vial and lyophilized in a conventional manner.

(2) Operation

200 $\mu$mof a serum sample was introduced into a 1.5 ml Eppendorf tube and 15 $\mu$mof the reagent A was added thereto, followed by stirring. The mixture was centrifuged and 100 $\mu$mof the supernatant was supplied to the pretreatment column, from which the cap and seal were removed, placed on a plastics tube. After the liquor had completely passed through the resin, 0.5 ml of distilled water was added thereto for washing. After washing with additional 0.5-ml portions of distilled water twice, 1.6 ml of an effluent from the pretreatment column was collected. The reagent B was regenerated by adding 100 ml of distilled water thereto. 0.5 ml of the regenerated reagent B was added to the above effluent through a tip provided with a filter for removing suspended matters. The obtained mixture was stirred and incubated at 37° C. for one hour. The absorbance of the reaction mixture at 405 nm was measured with a conventional spectrometer.

Separately, a standard 1,5-AG sample (40 $\mu$g/ml) was prepared by adding 5 ml of distilled water to a standard solution. Then a calibration curve was formed with the use of the standard sample, another standard sample obtained by diluting the same two-fold, and distilled water. Thus 1,5-AG in the serum sample was determined from the absorbance according to the calibration curve. The determination according to the calibration curve was carried out in the following manner. To 100 $\mu$mof the above standard, 1.5 ml of distilled water and 0.5 ml of the regenerated reagent B were added, followed by stirring. Then it was treated in the same manner as that employed in the case of the above effluent derived from a serum sample and the absorbance of the reaction mixture was measured. The same results as those of Example 5 were obtained by using this kit.

The present invention is closely related to the disclosure of our co-pending application Ser. No. 867,088 filed May 27, 1986. Accordingly, the specification, claims and drawings of said U.S. patent application Ser. No. 867,088 are hereby incorporated herein by this reference thereto. It is to be noted that, since the claims of said U.S. patent application Ser. No. 867,088 differ from those present application, one or more of the inventors named in said U.S. patent application Ser. No. 867,088 are not named as inventors of the present application, and one or more of the inventors named in the present application are not named as inventors of said U.S. patent application Ser. No. 867,088.

What is claimed is:

1. A reagent kit for assaying 1,5-anhydroglucitol which comprises, in separate containers, an agent for removing sugars, a reagent for detecting hydrogen peroxide, and an enzyme for oxidizing 1,5-anhydroglucitol, wherein said agent for removing sugars is a strongly basic anion exchange resin selected from the group consisting of an OH-form anion exchange resin and a borate anion exchange resin and wherein said enzyme for oxidizing 1,5-anhydroglucitol is pyranose oxidase or L-sorbose oxidase.

2. A reagent kit for assaying 1,5-anhydroglucitol as set forth in claim 1, which further comprises a cation exchange resin.

3. A regent kit for assaying 1,5-anhydroglucitol as set forth in claim 1, wherein said strongly basic anion exchange resin has a tri ($C_1$-$C_4$)-alkylamino group or a hydroxy ($C_1$-$C_4$) alkyldi ($C_1$-$C_4$)alkylamino group as an ion exchange group and has a particle size sufficient to pass through 200-to 400-mesh sieves.

4. A regent kit for assaying 1,5-anhydroglucitol as set forth in claim 1, wherein said borate type anion exchange resin has both di($C_1$-$C_4$)-alkylamino group and hydroxy ($C_1$-$C_4$)alkyl di($C_1$-$C_4$)-alkylamino group as an ion exchange group.

5. A reagent kit for assaying 1,5-anhydroglucitol as set forth in claim 1, which comprises:
   (1) a column packed with 0.1 to 1 ml of a strongly basic anion exchange resin and 0.01 to 0.5 ml of a cation exchange resin;
   (2) 10 m units to 100 units per sample of horseradish peroxidase,
       0.5 to 10 $\mu$M per sample of ABTS, and
       0.5 to 10 units per sample of pyranose oxidase;
   (3) 5–20 $\mu$g per sample of a perchloric acid solution; and
   (4) 0.1 to 1 mg of 1,5-anhydroglucitol.

6. A process for determining 1,5-anhydroglucitol, which comprises selectively removing sugars from a specimen containing 1,5-anhydroglucitol adding pyranose oxidase or L-sorbose oxidase to said sample in the presence of oxygen; detecting the amount of hydrogen peroxide formed as a result of enzymatic oxidation of 1,5-anhydroglucitol; anddetermining of 1,5-anhydroglucitol; and determining 1,5-anhydroglucitol from the amount of hydrogen peroxide thus formed.

7. A process for assaying 1,5-anhydroglucitol as set forth in claim 6, wherein said pyranose oxidase is produced by a microorganism belonging to the genus Polyporus while said L-sorbose oxidase is produced by a microorganism belonging to the genus Trametes.

8. A process for asaying 1,5-anhydroglucitol as set forth in claim 6, wherein 0.5 to 10 units per sample of pyranose oxidase or L-sorbose oxidase is allowed to act on 1,5-anhydroglucitol present in said sample at 4° to 50° C. for 0.5 to 3 hours.

9. A process for assaying 1,5-anhydroglucitol as set forth in claim 6, wherein sugars contained in said specimen are selectively removed by passing said specimen over a strongly basic anion exchange resin.

10. A process for assaying 1,5-anhydroglucitol as set forth in claim 9, wherein said sample, from which sugars have been selectively removed by passing said specimen over said strongly basic anion exchange resin, is neutralized by passing said sample over a cation exchange resin.

* * * * *